(12) United States Patent
Lin et al.

(10) Patent No.: US 11,547,824 B2
(45) Date of Patent: Jan. 10, 2023

(54) RESPIRATORY MASK

(71) Applicants: Shu-Chi Lin, New Taipei (TW);
Chih-Tsan Chien, New Taipei (TW);
Chun-Hung Chen, New Taipei (TW);
Sheng-Wei Lin, New Taipei (TW);
Pi-Kai Lee, New Taipei (TW);
Yu-Chen Liu, New Taipei (TW);
Chia-Wei Huang, New Taipei (TW)

(72) Inventors: Shu-Chi Lin, New Taipei (TW);
Chih-Tsan Chien, New Taipei (TW);
Chun-Hung Chen, New Taipei (TW);
Sheng-Wei Lin, New Taipei (TW);
Pi-Kai Lee, New Taipei (TW);
Yu-Chen Liu, New Taipei (TW);
Chia-Wei Huang, New Taipei (TW)

(73) Assignee: APEX MEDICAL CORP., New Taipei (TW)

( * ) Notice: Subject to any disclaimer, the term of this patent is extended or adjusted under 35 U.S.C. 154(b) by 416 days.

(21) Appl. No.: 16/563,966

(22) Filed: Sep. 9, 2019

(65) Prior Publication Data
US 2020/0086071 A1  Mar. 19, 2020

(30) Foreign Application Priority Data
Sep. 14, 2018  (TW) .............................. TW107132543

(51) Int. Cl.
*A61M 16/00* (2006.01)
*A61M 16/06* (2006.01)
*A61M 16/08* (2006.01)

(52) U.S. Cl.
CPC .... *A61M 16/0605* (2014.02); *A61M 16/0816* (2013.01)

(58) Field of Classification Search
CPC ...................... A61M 16/0605; A61M 16/0816
See application file for complete search history.

(56) References Cited

U.S. PATENT DOCUMENTS

| 7,011,090 B2* | 3/2006 | Drew | A61M 16/06 128/202.27 |
| 7,861,715 B2* | 1/2011 | Jones | A61M 16/06 128/204.21 |
| 8,539,953 B2* | 9/2013 | Moenning, Jr. | A61M 16/0816 128/206.21 |
| 8,550,084 B2* | 10/2013 | Ng | A61M 16/06 128/206.28 |
| 10,322,254 B2* | 6/2019 | Fong | A61M 16/0622 |

(Continued)

*Primary Examiner* — Steven O Douglas

(57) ABSTRACT

The present invention provides a respiratory mask comprising a nose cushion assembly. The nose cushion assembly comprises a base body and a buffering piece. The base body has a base intake portion, a base connection portion, and an air routing piece disposed at the inside of the base body and having a partitioning wall and a wall connection piece. The inside of the partitioning wall encloses an air intake zone. The wall connection piece is disposed outside the partitioning wall and connects with the base intake portion. Between the partitioning wall and the base intake portion there is defined an air outtake zone. The air intake zone is approximately at the center of the base intake portion. The buffering piece connects with the base connection portion and encloses a nose containing room, which in turn connects with the inside of the base body.

17 Claims, 15 Drawing Sheets

(56) References Cited

U.S. PATENT DOCUMENTS

| | | | |
|---|---|---|---|
| 10,653,854 B2* | 5/2020 | Prentice | A61M 16/0825 |
| 2010/0282264 A1* | 11/2010 | Chang | A61M 16/06 |
| | | | 128/206.21 |
| 2020/0353193 A1* | 11/2020 | Collins | A61M 16/06 |

* cited by examiner

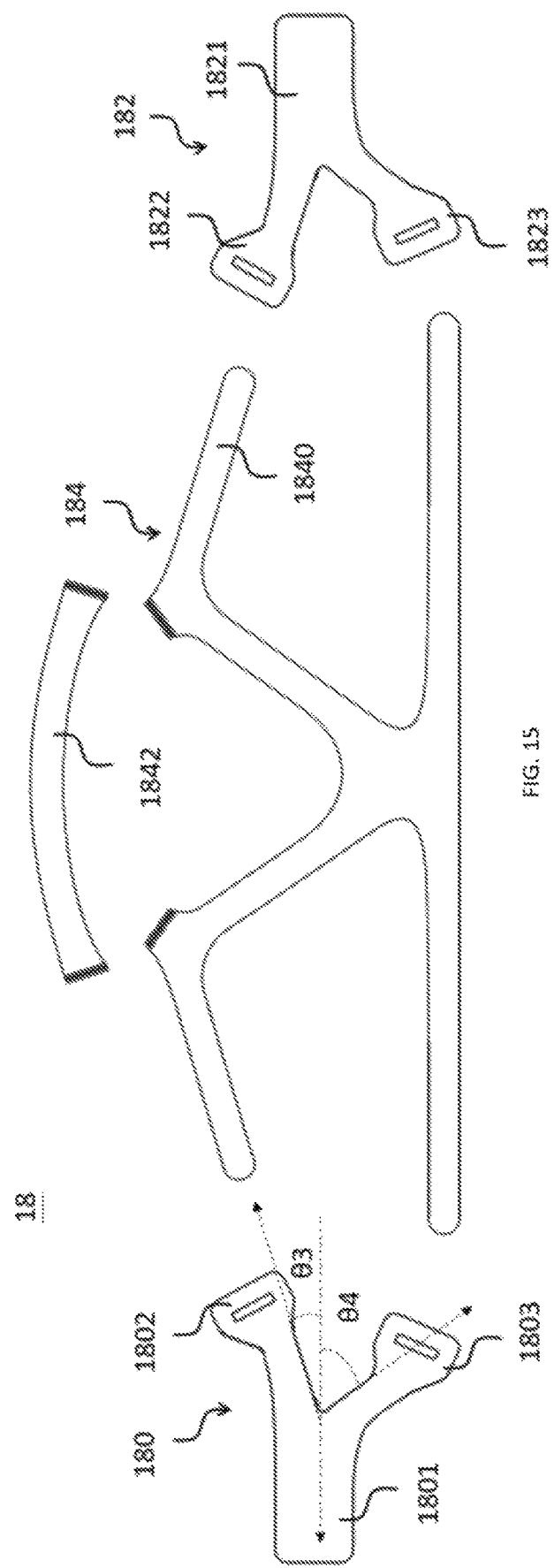

RESPIRATORY MASK

CROSS REFERENCE TO RELATED APPLICATION

The present application claims priority to Taiwan patent application Serial No. 107132543 filed on Sep. 14, 2018, the entire content of which is incorporated by reference to this application.

BACKGROUND OF THE INVENTION

1. Field of the Invention

The present invention pertains to a respiratory mask.

2. Description of the Prior Art

On the back of advances in medical engineering, many new medical apparatus are fabricated to counter diseases and syndromes. Patients are relieved of the effects of diseases by employing adequate medical apparatus. Someone with sleep apnea, for instance, could put on a respiratory mask before going to bed to improve his or her quality of sleep. Said respiratory mask must securely cover its wearer's mouth or nose, for it functions during sleep, and during sleep the wearer might inadvertently let loose the mask while turning over or through a random limb movement. Another major design concern with regard to the mask is comfort, for it is worn for long periods of time.

SUMMARY OF THE INVENTION

The present invention provides a respiratory mask that includes a ventilating portion to facilitate the airflow within the mask, thus reducing the discomfort caused by long-time usage.

The present invention provides a respiratory mask comprising an air pipe assembly. The air pipe assembly comprises a first connection portion, on which there are defined a first surface, a lateral facet, and a second surface. The first connection portion has a first ventilating portion and a second ventilating portion. The first and second ventilating portions stretch from the first surface to the second surface. The first surface is adjacent to the lateral facet. The first and second ventilating portions are symmetrically disposed within the first connection portion and are exposed at the first surface and the lateral facet.

The present invention provides a respiratory mask wherein a ventilating portion is rotatable relative to a shell, thereby facilitating the airflow within the mask and reducing the discomfort caused by long-time usage.

The present invention provides a respiratory mask comprising an air pipe assembly and a shell. The air pipe assembly comprises a curved pipe body and a first connection portion. An end of the curved pipe body connects with the first connection portion. The first connection portion has a first through hole, a first positioning portion, and a first ventilating portion. Together the curved pipe body and the first through hole form an air passage. The shell comprises a second positioning portion rotatably mounted at the first positioning portion. The first ventilating portion rotates relative to the shell and the curved pipe body rotates relative to the shell when the first positioning portion rotates relative to the second positioning portion.

The present invention provides a respiratory mask that is more comfortable to wear on a head, reduces the possibility that the wearer let loose the mask through an inadvertent touch, and can be taken off and disassembled quickly.

The present invention provides a respiratory mask comprising a first bent plate, a second bent plate, and a head strap assembly. A first ring portion is disposed at one end of the first bent plate; a first slot is disposed at another end of the first bent plate. A second ring portion is disposed at one end of the second bent plate; a second slot is disposed at another end of the second bent plate. The head strap assembly comprises a first supporting strap and a second supporting strap. The first supporting strap has a first branch, a second branch, and a third branch. The first branch connects respectively with the second and third branches, and is detachably connected to the first ring portion. The directions by which the first and second branches respectively stretch form a first strap angle; the directions by which the first and third branches respectively stretch form a second strap angle. The second supporting strap has a fourth branch, a fifth branch, and a sixth branch. The fourth branch connects respectively with the fifth and sixth branches, and is detachably connected to the second ring portion. The directions by which the fourth and fifth branches respectively stretch form the first strap angle; the directions by which the fourth and sixth branches respectively stretch form the second strap angle. The first and second strap angles amount to less than 90°.

The present invention provides a respiratory mask that includes a nose cushion assembly. The nose cushion assembly includes an air routing piece to facilitate the airflow within the mask, thus reducing the discomfort caused by long-time usage.

The present invention provides a respiratory mask comprising a nose cushion assembly. The nose cushion assembly comprises a base body and a buffering piece. The base body is defined as having a base intake portion and a base connection portion. The base body comprises an air routing piece disposed at the inside of the base body and having a partitioning wall and a wall connection piece. The inside of the partitioning wall encloses an air intake zone. The wall connection piece is disposed outside the partitioning wall and connects with the base intake portion. Between the partitioning wall and the base intake portion there is defined an air outtake zone. The air intake zone is approximately at the center of the base intake portion. The buffering piece connects with the base connection portion and encloses a nose containing room, which in turn connects with the inside of the base body.

In some embodiments, the first connection portion could further comprise a second ventilating portion, the first ventilating portion and the second ventilating portion are symmetrically disposed within the first connection portion. On the first connection portion there are defined a first surface, a lateral facet, and a second surface, the first surface could be adjacent to the lateral facet; and the first ventilating portion and the second ventilating portion could stretch from the first surface to the second surface and are exposed at the first surface and the lateral facet. Besides, on the first connection portion there is further defined an incline adjacent to the lateral facet, the lateral facet could be between the first surface and the incline, and the first ventilating portion could be exposed at the incline. The first ventilating portion could be more exposed at the first surface than at the incline.

In some embodiments, the first connection portion has further a first positioning portion and a first blocking portion, the first positioning portion could be exposed at the lateral facet, the first blocking portion could be disposed at the first surface, and the first positioning portion and the first blocking portion could be at different sides of the first surface.

Besides, the shell could further comprise a second positioning portion rotatably mounted at the first positioning portion, the first ventilating portion rotates relative to the shell and the curved pipe body rotates relative to the shell when the first positioning portion rotates relative to the second positioning portion. Furthermore, the first blocking portion could stretch from the first surface, and part of the first blocking portion could be outside the perimeter of the first surface.

To summarize: The present invention provides a respiratory mask that is more comfortable to wear and wherein the airways and circulation are improved. The respiratory mask as provided can securely cover its user's mouth or nose, reduce the possibility that the user let loose the mask through an inadvertent touch, and can be taken off and disassembled quickly.

BRIEF DESCRIPTION OF THE APPENDED DRAWINGS

FIG. 15 is a diagram of a head strap assembly, in accordance with an embodiment of the present invention.

DETAILED DESCRIPTION OF THE INVENTION

The features, objectives, and functions of the present invention are further disclosed below. However, it is only a few of the possible embodiments of the present invention, and the scope of the present invention is not limited thereto; that is, the equivalent changes and modifications done in accordance with the claims of the present invention will remain the subject of the present invention. Without departing from the spirit and scope of the invention, it should be considered as further enablement of the invention.

Figure 1:
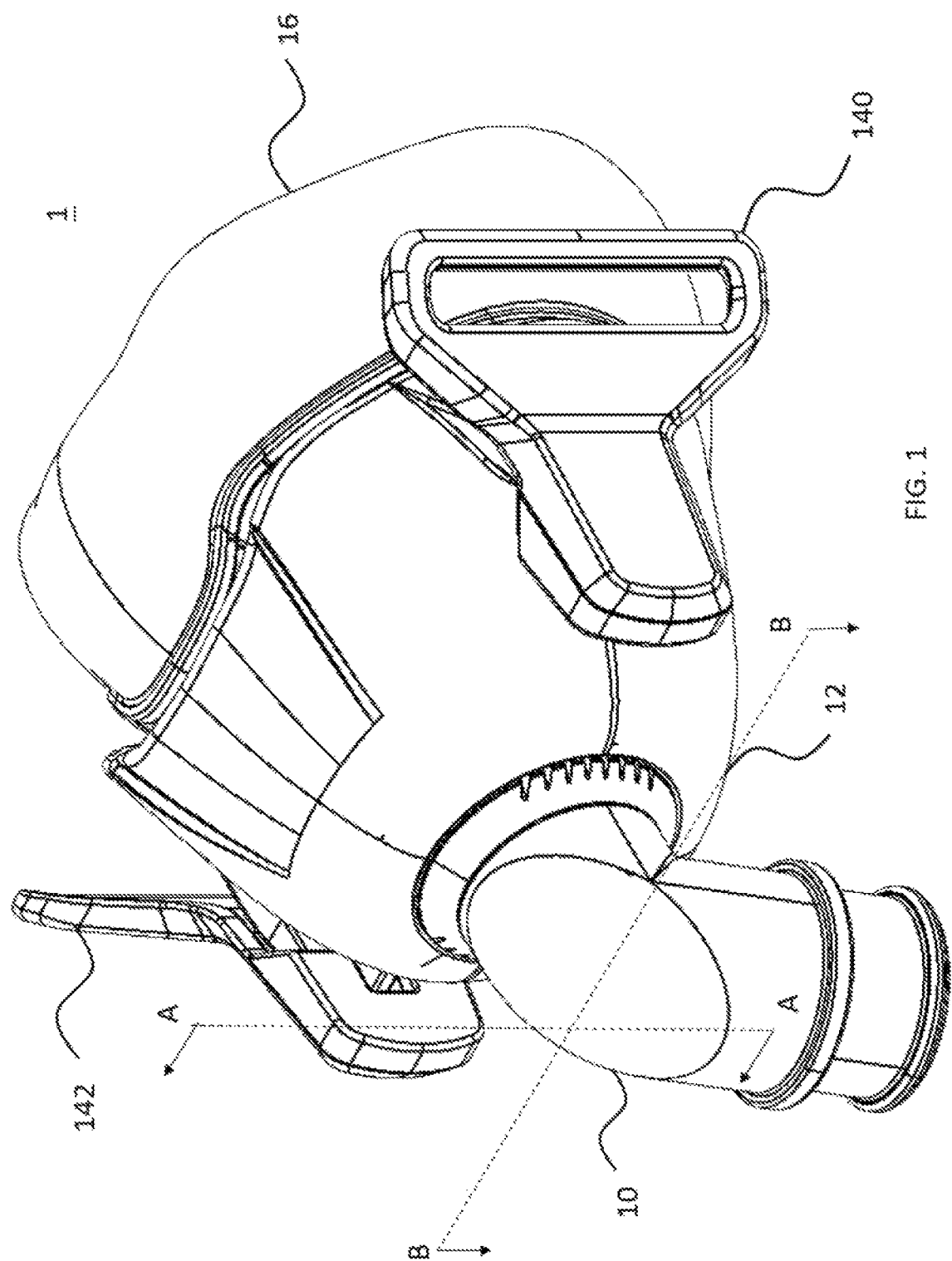
FIG. 1 is a stereogram of a respiratory mask, in accordance with an embodiment of the present invention.

Please refer to FIG. 1, a stereogram of a respiratory mask in accordance with an embodiment of the present invention.

As depicted in FIG. 1, the respiratory mask 1 comprises an air pipe assembly 10, a shell 12, a bent plate 140 (first bent plate), a bent plate 142 (second bent plate), and a nose cushion assembly 16. The air pipe assembly 10 is connected to the shell 12, and so is the nose cushion assembly 16. The bent plates 140 and 142 are connected to opposite sides of the shell 12. The present embodiment does not prescribe how exactly the air pipe assembly 10, the bent plates 140 and 142, and the nose cushion assembly 16 are connected to the shell 12. Any of the connections may be a contact means that is temporary or non-stationary, say a pivot with relative rotation, a detachable mortise-and-tenon pair, or a general joggle joint. Any of the connections may alternatively be a contact means that is relatively fixed and permanent, such as by adhesion, locking, welding, or monolithic molding.

In addition to being connected to the shell 12, the bent plates 140 and 142 under normal usage may be connected to a head strap assembly (not shown in FIG. 1), so that the user's head is more or less fastened between the head strap assembly and the shell 12. The nose cushion assembly 16 may be in direct contact with the user's nasal area. In one example, the air pipe assembly 10 is connected to an external air supply (not shown in FIG. 1). The breathable air blown out of the external supply is directed into the nose cushion assembly 16 through the air pipe assembly 10 and the shell 12 to reach the user. The air from the external supply slightly raises the pressure inside the nose cushion assembly 16, thus making it easier for the user to inhale. The present embodiment is identified by the fact that the bent plates 140 and 142 may be connected to the head strap assembly, and that the nose cushion assembly 16 may be assembled with the shell 12, while in practice the sizes of the hand strap assembly and the nose cushion assembly 16 are up to the bodily proportions of the user. To illustrate in detail the construction and functionality of the respiratory mask 1, each of its components is described hereinbelow.

Figure 2:
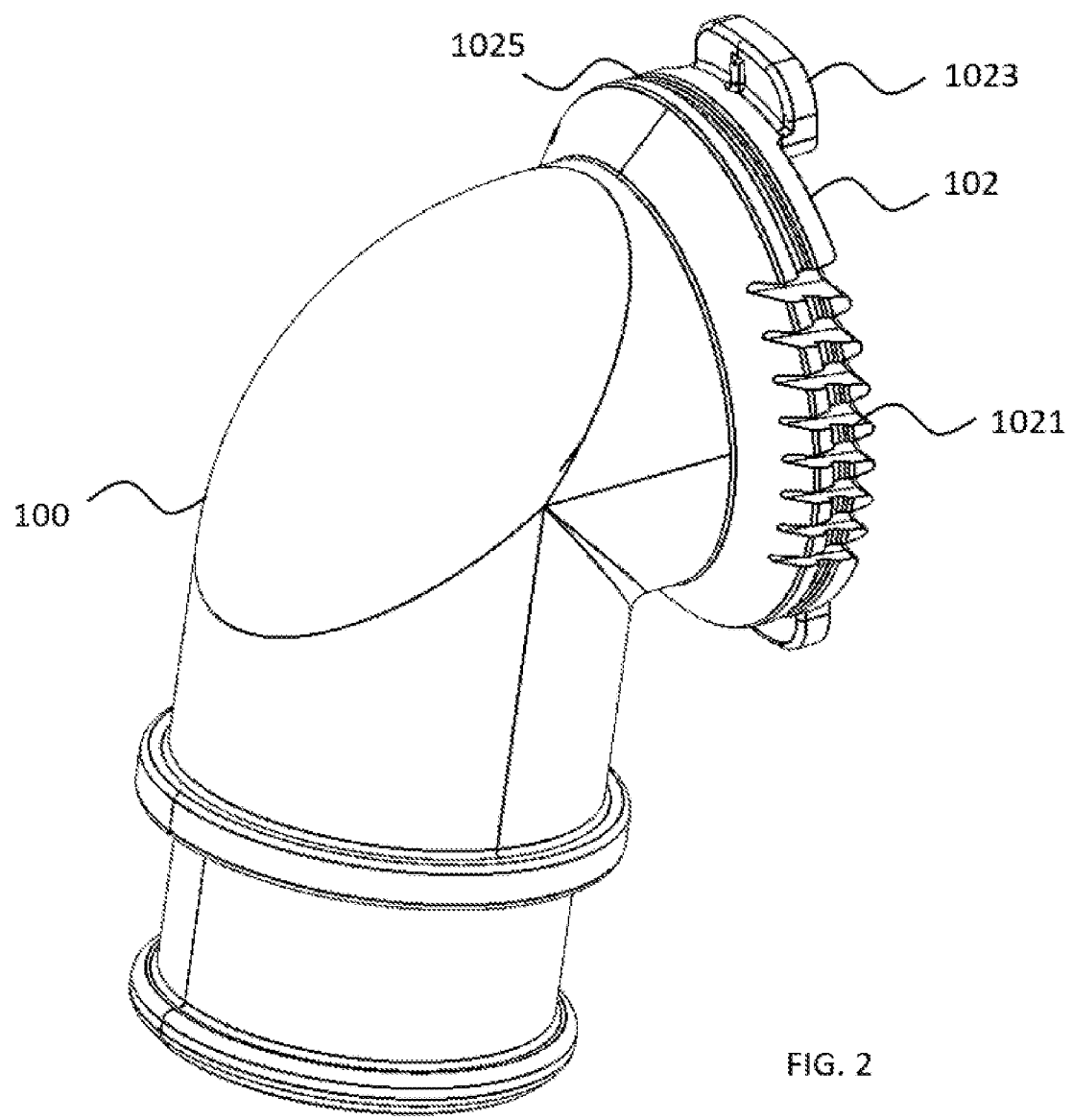
FIG. 2 is a stereogram of an air pipe assembly, in accordance with an embodiment of the present invention.
Figure 3:
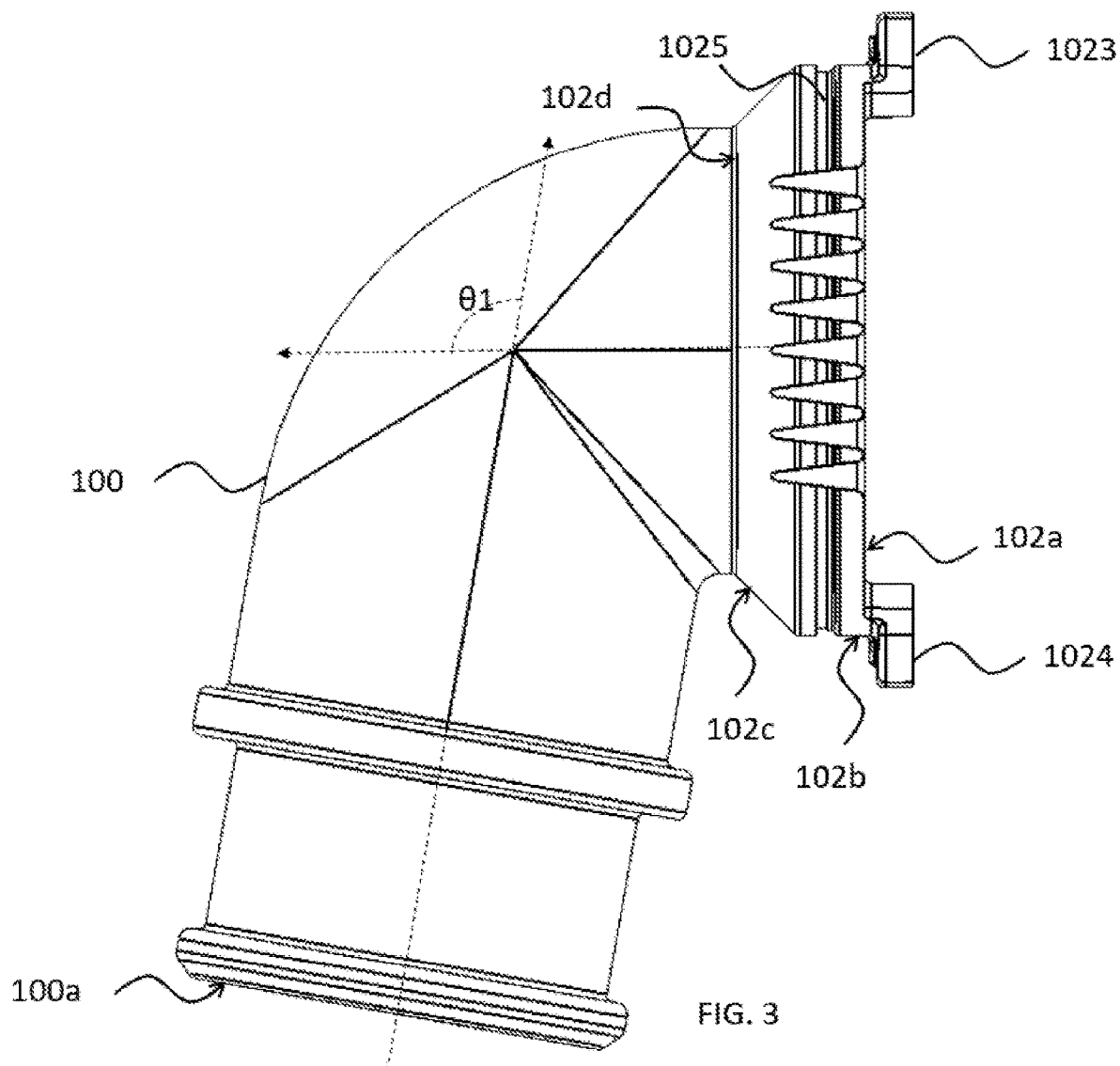
FIG. 3 is a side view of an air pipe assembly, in accordance with an embodiment of the present invention.
Figure 4:
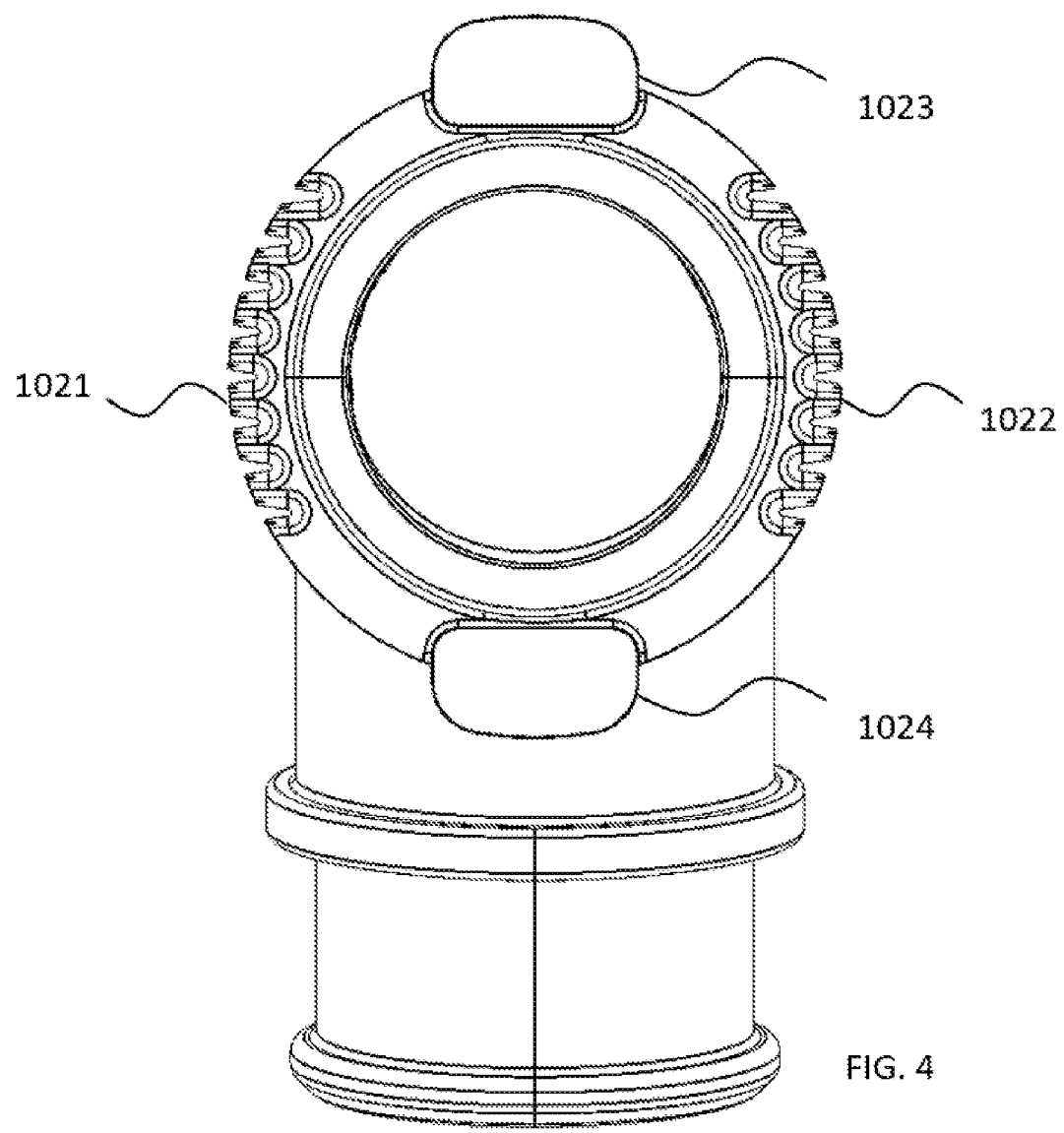
FIG. 4 is a front view of an air pipe assembly, in accordance with an embodiment of the present invention.

Please refer to FIGS. 1 through 4 in conjunction. In accordance with an embodiment of the present invention, FIGS. 2, 3, and 4 are a stereogram, a side view, and a front view of an air pipe assembly, respectively. As depicted in the figures, the air pipe assembly 10 has a curved pipe body 100 and a connection portion 102 (first connection portion). Situated at one end of the curved pipe body 100, the connection portion 102 may include a ventilating portion 1021 (first ventilating portion), a ventilating portion 1022 (second ventilating portion), a blocking portion 1023 (first blocking portion), a blocking portion 1024 (second blocking portion), and a positioning portion 1025 (first positioning portion). In one example, the connection portion 102 is affixed to the curved pipe body 100; in another, the curved pipe body 100 and the connection portion 102 are molded monolithically. The present embodiment does not prescribe of what the air pipe assembly 10 is made. The connection portion 102 is structurally complex; to uphold the rigidity of that structure, a harder plastic material may be suitable for fabricating an air pipe assembly 10 where the curved pipe body 100 and the connection portion 102 are monolithically formed.

For the sake of clarity, there are a number of surfaces defined on the connection portion 102, e.g. the first surface 102a, the lateral facet 102b, the incline 102c, and the second surface 102d. One end of the curved pipe body 100 is in contact with the second surface 102d, whereas at another end of the curved pipe body 100 there is defined a third surface 100a. In practice, the curved pipe body 100 may be a hollow tubular structure, connected to a hose via the third surface 100a. The hose is in turn connected to an external air supply, which pumps air into the hollow curved pipe body 100 and further into the nose cushion assembly 16. The pipe angle θ1, by which the curved pipe body 100 curves, can be defined in terms of the aforesaid surfaces. Here the pipe angle θ1 may be the angle formed between the normal directions of the second surface 102d and the third surface 100a. The pipe angle θ1 may fall within a range, whose lower bound may be 100°, 103°, 105°, 108°, or 110°, and whose upper bound may be 125°, 128°, 130°, 133°, or 135°.

It is inferable from the figures that the perimeters of the first surface 102a and the second surface 102d are each approximately circular, and that the area enclosed by the perimeter of the first surface 102a is larger than that enclosed by the perimeter of the second surface 102d. The connection portion 102 appears to be greater in diameter than the curved pipe body 100 as a result. Along the perimeter of the first surface 102a can be found, in clockwise order, the blocking portion 1023, the ventilating portion 1022, the blocking portion 1024, and the ventilating portion 1021. In other words, the ventilating portions 1021 and 1022 are each situated between two blocking portions; the distance between either blocking portion 1023 or 1024 and either ventilating portion 1021 or 1022 is less than that between two blocking portions. In one example, the ventilating portions are symmetrical, and so are the blocking portions; therefore, the blocking portions 1023 and 1024 are equidistant from any of the ventilating portions 1021 and 1022.

In one example, the pipe angle θ1 of the curved pipe body 100 is slightly greater than 90° to better facilitate the airflow and reflect a real-world scenario. When the user lies on his or her back wearing the respiratory mask 1 and the pipe angle θ1 is 90° or less, the hose to which the curved pipe body 100 is connected might hang across the user's mouth or face and cause discomfort. On the contrary, when the pipe angle θ1 is slightly greater than 90°, say 105°, the hose may be stretched in such a direction that there is less chance of it hanging across the user's mouth or face, thereby improving his or her quality of sleep.

Please refer to FIGS. 1 through 4 still. On the connection portion 102 there are disposed the ventilating portions 1021 and 1022, which are configured to facilitate the airflow. Specifically, when the air pipe assembly 10 is assembled with the shell 12, air may flow from one side of the shell 12 to another side through the ventilating portions 1021 and 1022. In one example, the ventilating portions 1021 and 1022 each have concavities; in other words, adjacent concavities are grouped and defined as either ventilating portion 1021 or 1022. The ventilating portions 1021 and 1022 may be exposed at the first surface 102a, the lateral facet 102b, and the incline 102c, so that air is guided by the ventilating portions 1021 and 1022 from beside the first surface 102a to beside the incline 102c via the lateral facet 102b, or vice versa.

In practice, said concavities can be seen as through holes drilled from the first surface 102a. The through holes are centered near the perimeter of the first surface 102a; they look like concavities chipped on the lateral facet 102b as a result. With respect to the present embodiment, the through holes are of arbitrary diameters, need not be round, and the centers of those holes are arbitrarily close to the perimeter of the first surface 102a. It is perfectly practical that the through holes do not break out of the lateral facet 102b. The orientation of the through holes, i.e. the drill direction, may not be the same as the normal direction of the first surface 102a. For instance, FIG. 3 shows oblique holes drilled toward the lateral facet 102b, giving the ventilating portion 1021 larger openings at the first surface 102a than at the incline 102c.

The positioning portion 1025 may also be a concavity, say a groove structure. The ventilating portion 1021 or 1022 may be exposed at the lateral facet 102b; therefore, the opening of the positioning portion 1025 may overlap those of the ventilating portion 1021 or 1022 at the lateral facet 102b. As depicted in FIG. 2, when the positioning portion 1025 and the ventilating portion 1021 overlap, the latter does not constitute a plane along the lateral facet 102b, a fact that usually does not affect or compromise the ventilation. In one example, the positioning portion 1025 stretches over the full circle of the lateral facet 102b; since the ventilating portion 1021 is seldom disposed on the whole of the lateral facet 102b, the aggregate area of the openings of the ventilating portion 1021 at the lateral facet 102b is usually less than or equal to the area of the opening of the positioning portion 1025 at the same.

The ventilating portions 1021 and 1022 may be symmetrical structures. Their symmetry corresponds to real-world scenarios. Say the ventilating portions 1021 and 1022 are on opposite sides of the connection portion 102 and away from the direction along which the curved pipe body 100 stretches. It is less likely, then, that both are obscured by the aforesaid hose and that the airflow is hampered. Even if one of the ventilating portions 1021 and 1022 was obscured by the hose because of the user's particular pose (e.g. lying on his or her side), the other ventilating portion, the one on the opposite side, could still function and facilitate the airflow.

Figure 5:
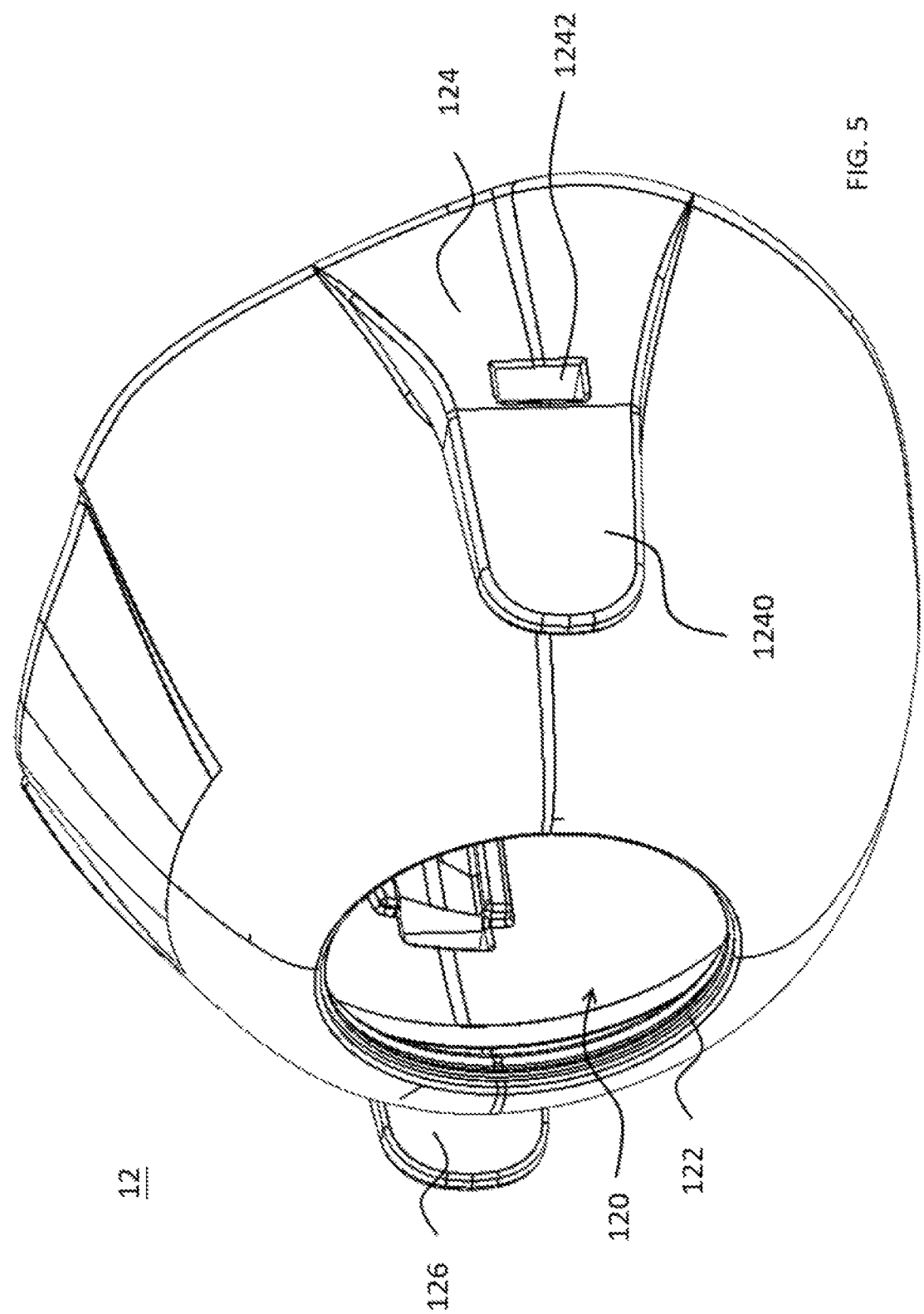
FIG. 5 is a stereogram of a shell, in accordance with an embodiment of the present invention.
Figure 6:
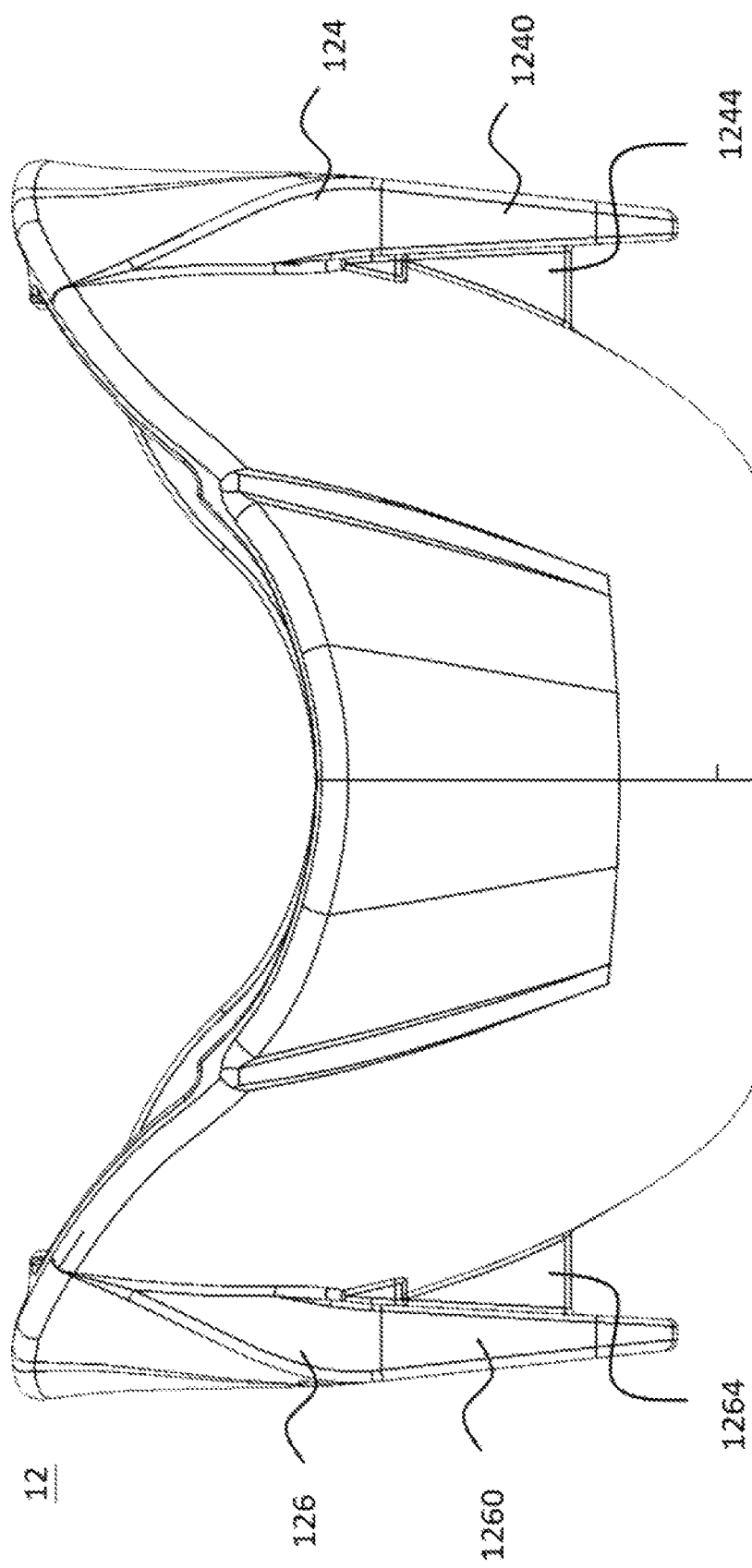
FIG. 6 is a bird's-eye view of a shell, in accordance with an embodiment of the present invention.
Figure 7:
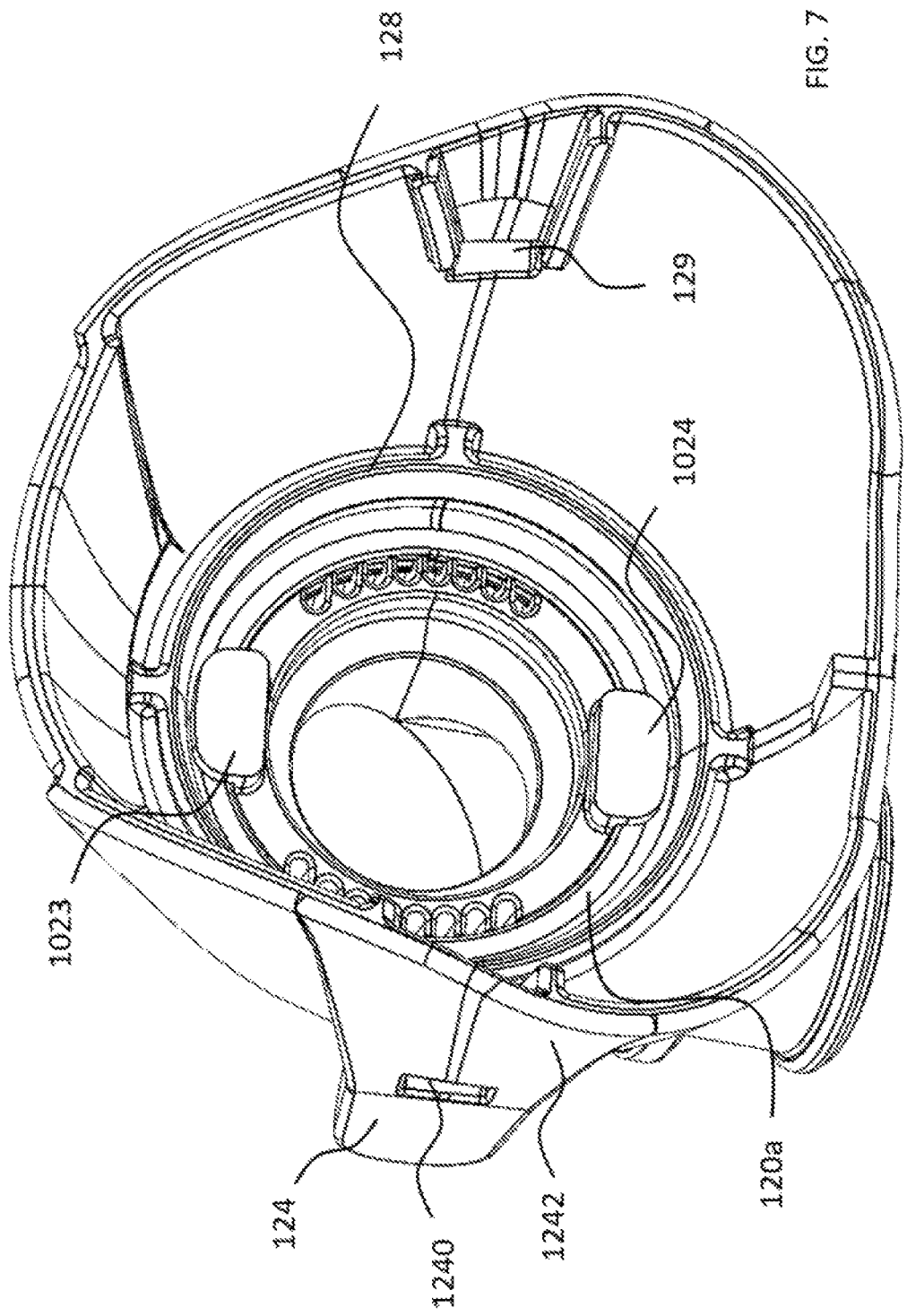
FIG. 7 is a stereogram of a shell and an air pipe assembly, in accordance with an embodiment of the present invention.

The connection portion 102 includes the blocking portions 1023 and 1024 and the positioning portion 1025 to joggle together the air pipe assembly 10 and the shell 12 and to allow the air pipe assembly 10 to rotate relative to the shell 12. For distilled illustration of the relativity between the shell 12 and the air pipe assembly 10, please refer to FIGS. 5 through 7 in conjunction. In accordance with an embodiment of the present invention, FIGS. 5 and 6 are a stereogram and a bird's-eye view of a shell, respectively, and FIG. 7 is a stereogram of a shell and an air pipe assembly. As depicted in the figures, a through hole 120 (second through hole), a positioning portion 122 (second positioning portion), a buckling portion 124 (first buckling portion), and a buckling portion 126 (second buckling portion) are visible on the outside of and included as part of the shell 12, an approximate hemisphere. If the area with the largest opening is called the bottom, then the through hole 120 is situated roughly at the zenith, or the center of the top, of the shell 12, acting as a duct connecting the interior and exterior of the shell 12. The positioning portion 122 is disposed on the wall of the through hole 120. In one example, the positioning portion 122 is an annular structure bulging into the duct. The present invention of course welcomes discretion in this regard. The positioning portion 122 may alternatively be a concavity sunk in the wall of the through hole 120.

In practice, the connection portion 102 may be contained in the midst of the through hole 120, the former's positioning portion 1025 joggled with the positioning portion 122. The positioning portion 122 can thereby rotate relative to the positioning portion 1025; in other words, the positioning portion 122 is rotatably mounted at the positioning portion 1025, enabling the shell 12 to rotate relative to the air pipe assembly 10. Meanwhile, a supporting plane 120a (first supporting plane) is found inside the shell 12, close to the through hole 120. The supporting plane 120a is essentially an annular surface encircling the through hole 120. When the air pipe assembly 10 is assembled with the shell 12, the positioning portions 1025 and 122 are joggled, the blocking portions 1023 and 1024 are situated inside the shell 12, and the curved pipe body 100 is outside the shell 12. In one example, the blocking portions 1023 and 1024 are at least partly in contact with the supporting plane 120a, so as to prevent the air pipe assembly 10 from being pulled out of the shell 12. In another example, the joggle joint of the positioning portions 1025 and 122 are secure enough that the air pipe assembly 10 cannot be pulled out of the shell 12 even without the blocking portions 1023 and 1024. Both recent examples are feasible under the present embodiment, among others.

When the air pipe assembly 10 is assembled with the shell 12, the first surface 102a is on the same side as the inner surface of the shell 12, and the incline 102c is on the same side as the outer surface of the shell 12. In other words, the ventilating portions 1021 and 1022 form an air passage connecting the interior and exterior of the shell 12. Meanwhile, the blocking portions 1023 and 1024 are disposed at the first surface 102a, their undersides touching the supporting plane 120a; in one example, therefore, the first surface 102a and the supporting plane 120a are approximately coplanar.

Outside the shell 12 there are the buckling portions 124 and 126 opposite each other. The buckling portions 124 and 126 may be monolithically molded with the shell 12, or adhered, joggled, or locked onto the shell 12; the present embodiment welcomes discretion in this regard. Meanwhile, taking one of the buckling portions 124 and 126 for example, the buckling portion 124 includes a tongue 1240 (first tongue), a concavity 1242 (first concavity), and an aligning piece 1244 (first aligning piece). The concavity 1242 may be disposed at the upper side or outer surface of the tongue 1240, and the aligning piece 1244 at the lower side or inner surface of the same. In terms of the figures, the tongue 1240 may jut out of the shell 12 and stretch for a length. Shape-wise, the tongue 1240 may be wider and thicker at the end that connects with the shell 12, and narrower and thinner at the other end that is farther away from the shell 12. The present embodiment does not prescribe the actual dimensions of the tongue 1240. Furthermore, as the tongue 1240 only touches the shell 12 at one end, there is naturally a gap between the shell 12 and the part of the tongue 1240 that stretches away from it. Said aligning piece 1244 is situated within that gap; by definition, the concavity 1242 and the aligning piece 1244 are at different sides of the tongue 1240. In one example, the tongue 1240 stretches out of the shell 12 along a certain direction that may be parallel with the normal direction of the first surface 102a. Recall that the first surface 102a and the supporting plane 120a may be coplanar. That certain direction may therefore parallel the normal direction of the supporting plane 120a as well.

Seen from the interior, the shell 12 further includes an airtight structure 128 and a base positioning slot 129. The airtight structure 128, an approximate annular structure encircling the through hole 120, is disposed outside of the perimeter of the supporting plane 120a and configured to be in contact with the nose cushion assembly 16. Although the base positioning slot 129 as depicted in the figures is at a different side from the buckling portion 124, there may well be another base positioning slot (obscured by the other structures shown) that is at the same side as the buckling portion 124 and mirrors the base positioning slot 129 in terms of shape and structure. The base positioning slot 129 may be a concavity that opens on the inside of the shell 12, configured to be joggled with the nose cushion assembly 16.

In practice, the base positioning slot 129 may alternatively be a through hole that at one end opens on the inside of the shell 12, and at the other is exposed at the buckling portions 124 and 126, i.e. the concavity 1242 and a second concavity mirroring it in terms of construction. In other words, the base positioning slot(s) and the concavities of the buckling portions 124 and 126 may be the same hole. The functionality of the airtight structure 128 and the base positioning slot 129 is described hereinbelow along with the nose cushion assembly 16.

Figure 8:
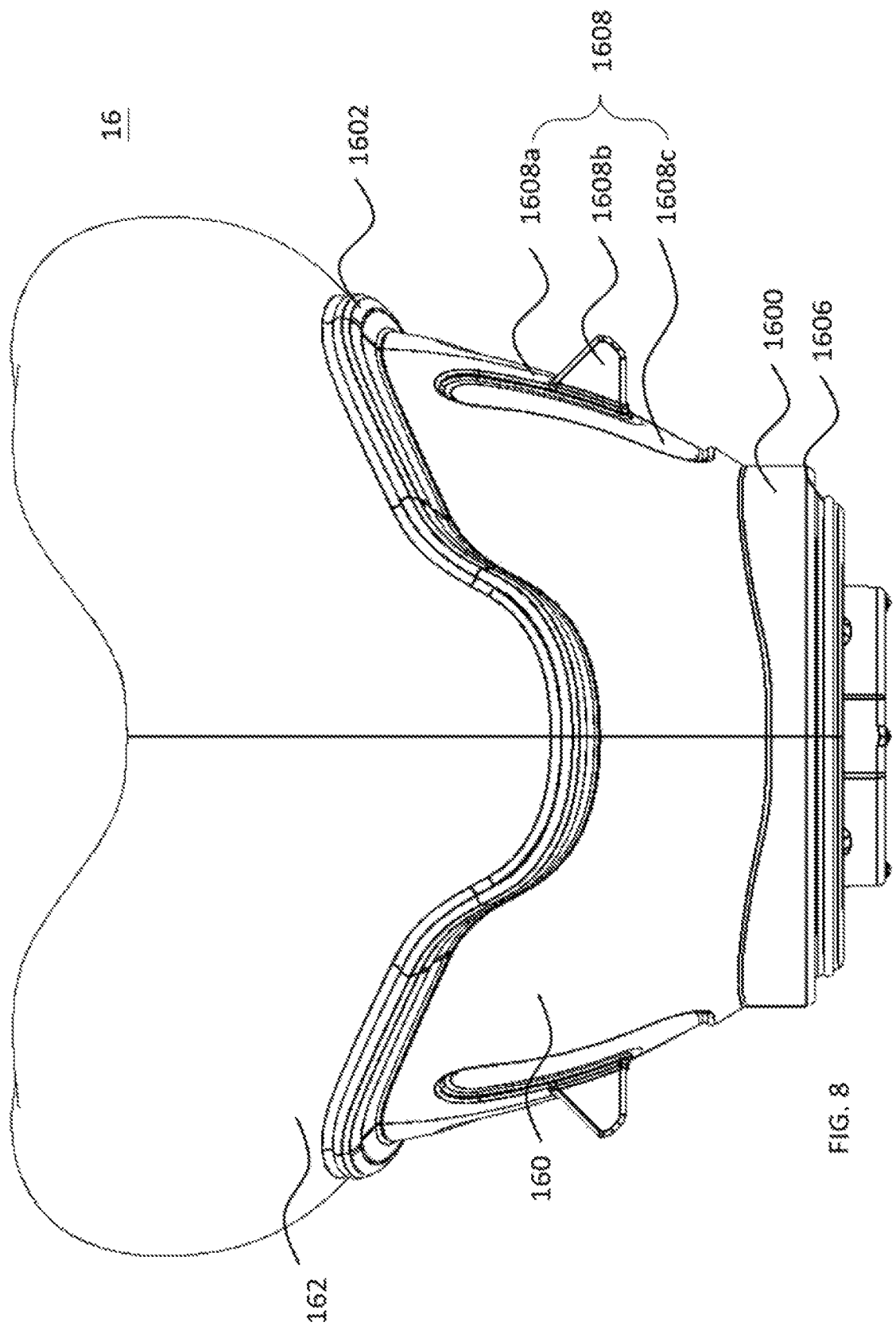
FIG. 8 is a bird's-eye view of a nose cushion assembly, in accordance with an embodiment of the present invention.
Figure 9:
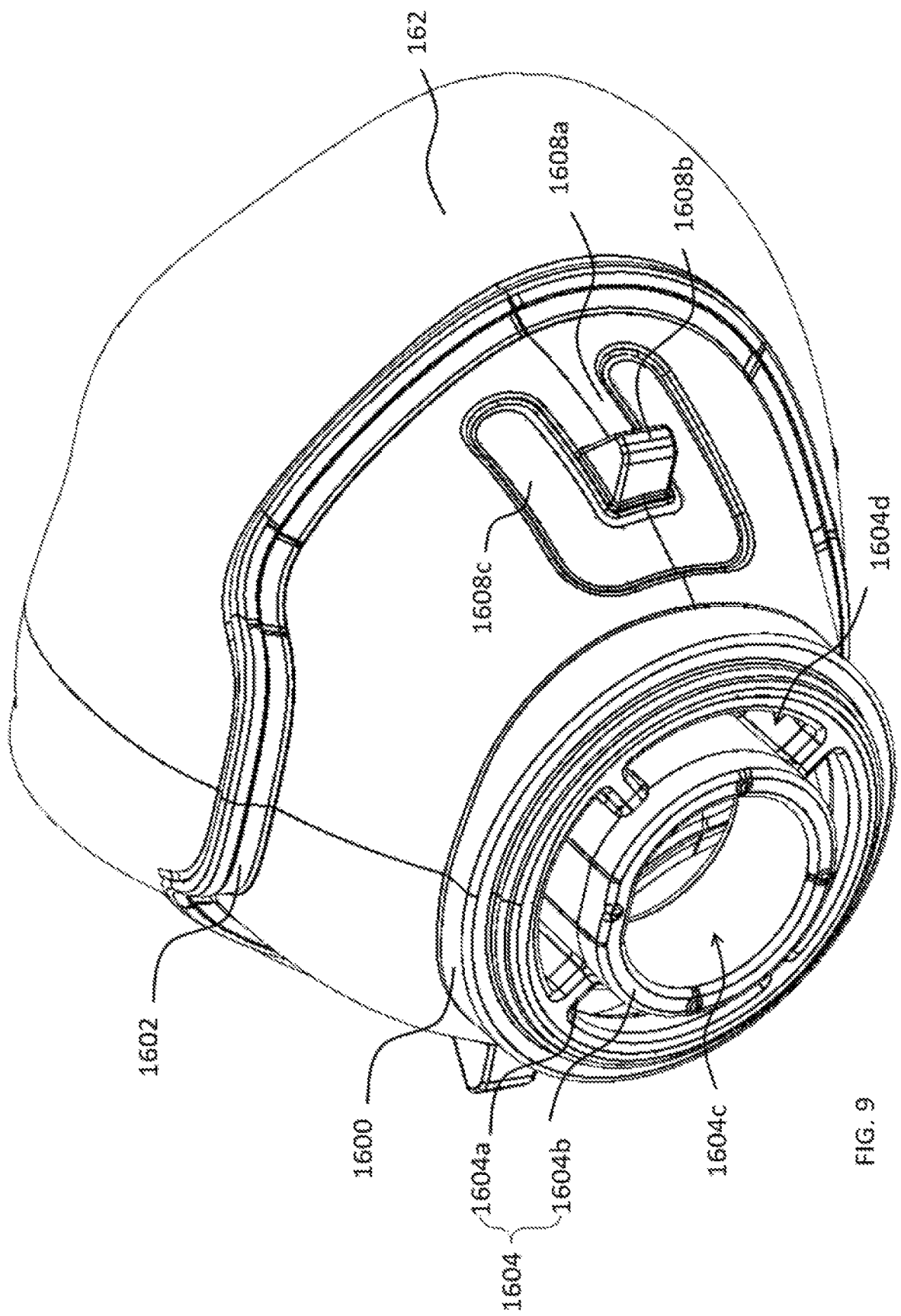
FIG. 9 is a stereogram of a nose cushion assembly, in accordance with an embodiment of the present invention.

Please refer to FIGS. 8 and 9 in conjunction. In accordance with an embodiment of the present invention, FIGS. 8 and 9 are a bird's-eye view and a stereogram of a nose cushion assembly, respectively. As depicted in the figures, the nose cushion assembly 16 includes a base body 160 and a buffering piece 162. The base body 160 is defined as having a base intake portion 1600 and a base connection portion 1602. Adjacent to the base intake portion 1600 is an air routing piece 1604 and an airtight ring body 1606. Between the base intake portion 1600 and the base connection portion 1602 is a base positioning piece 1608. The base connection portion 1602 connects the base body 160 and the buffering piece 162.

In one example, the nose cushion assembly 16 is fabricated heterogeneously. The base body 160 may be of a hard plastic, for instance, and the buffering piece of a soft one. In practice, the base body 160 and the air routing piece 1604 may be fabricated first with the same material. Soft compounds are then applied around the base intake portion 1600 and may be employed to yield the supple airtight ring body 1606. Finally, the supple buffering piece 162 is attached to the base connection portion 1602. In another example, the base body 160 and the buffering piece 162 are fabricated in one go. The present embodiment does not prescribe the order in which the components of the nose cushion assembly 16 are made.

The base intake portion 1600 may be connected to the air routing piece 1604, which is disposed inside the base body 160 and includes a partitioning wall 1604b and a wall connection piece 1604a. In one example, the partitioning wall 1604b delineates an air intake zone 1604c, and is connected to the base intake portion 1600 via the wall connection piece 1604a. The wall connection piece 1604a is of a certain width; therefore, there is a gap between the partitioning wall 1604b and the base intake portion 1600. That gap may be annular or arcuate, and may be defined as the air outtake zone 1604d. In practice, the air intake zone 1604c is situated roughly at the midst of the base intake portion 1600, whereas the air outtake zone 1604d is on the outside of the air intake zone 1604c.

The partitioning wall 1604b may be configured to separate air passages, but is not necessarily situated inside the shell 12. In one example, within the base intake portion 1600 there is defined an intake plane. The airtight ring body 1606 and the intake plane are approximately coplanar; thus there is no airflow beyond the intake plane. Here the airtight ring body 1606 may be disposed outside the base body 160, encircling the base intake portion 1600. Moreover, part of the partitioning wall 1604b may jut out of the base body 160 past the intake plane. When the nose cushion assembly 16 and the air pipe assembly 10 is assembled with the shell 12, part of the partitioning wall 1604b may even pass through the shell 12 and connect directly with the curved pipe body 100. In other words, together the curved pipe body 100, the through hole 120, and the air intake zone 1604c form an intake air passage.

In actual operation, the air pipe assembly 10 is connected to an air supply, which blows out air with a certain amount of pressure. Most of the pressurized air is directed through the hollow curved pipe body 100 into the air intake zone 1604c, and further into the nose cushion assembly 16. When the user puts on the respiratory mask 1, his or her nose is placed in a nose containing room (not numbered in the figures) enclosed by the buffering piece 162. Said nose containing room is not closed; it connects with the inside of the base body 160, and the combined space stretches to the curved pipe body 100.

When the user inhales, said pressurized air flows straight into the nasal cavity and opens up the respiratory tract. When the user exhales, the airflow let out enters the air outtake zone 1604d and is then directed outside the nose cushion assembly 16. In one example, the air outtake zone 1604d corresponds to the ventilating portions 1021 and 1022; the air exhaled leaves the respiratory mask 1 via the ventilating portions 1021 and 1022, which are adjacent to the air outtake zone 1604d. In other words, together the ventilating portions 1021 and 1022 and the air outtake zone 1604d associated with the air routing piece 1604 form an outtake air passage. The air routing piece 1604 adequately separates the intake and outtake air passages, making it easier for the user to breathe.

Please refer to FIGS. 7 through 9 in conjunction. The base body 160 may include a symmetrical duo (or more) of base positioning pieces 1608. A base positioning piece may comprise a positioning cantilever 1608a and a base positioning buckle 1608b. The base positioning buckle 1608b is disposed at the positioning cantilever 1608a, which in turn is connected to the outside of the base body 160. There may also be a buffering pad 1608c tucked underneath the positioning cantilever 1608a and disposed inside the base body 160. In one example, the buffering pad 1608c and the buffering piece 162 are made of the same material and joined together.

In actual operation when assembling the nose cushion assembly 16 with the shell 12, it may suffice to joggle the base positioning piece(s) 1608 and the base positioning slot(s) 129, i.e. to lodge the base positioning buckle 1608b in the base positioning slot 129 so that the nose cushion assembly 16 does not fall away from the shell 12 without prompt. Of course, the number of the base positioning pieces 1608 and the number of the base positioning slots 129 should match, in that one base positioning piece 1608 corresponds to one base positioning slots 129. To detach the nose cushion assembly 16 from the shell 12, the user may push the positioning cantilever 1608a inward until the base positioning buckle 1608b slides out of the base positioning slot 129. In one example where the buffering pad 1608c and the buffering piece 162 are joined, the user may squeeze the area of the buffering piece 162 close to the positioning cantilever 1608a instead of the positioning cantilever 1608a itself, to eject the base positioning buckle 1608b from the base positioning slot 129 by the motion of the buffering pad 1608c exerted on the positioning cantilever 1608a.

Figure 10:
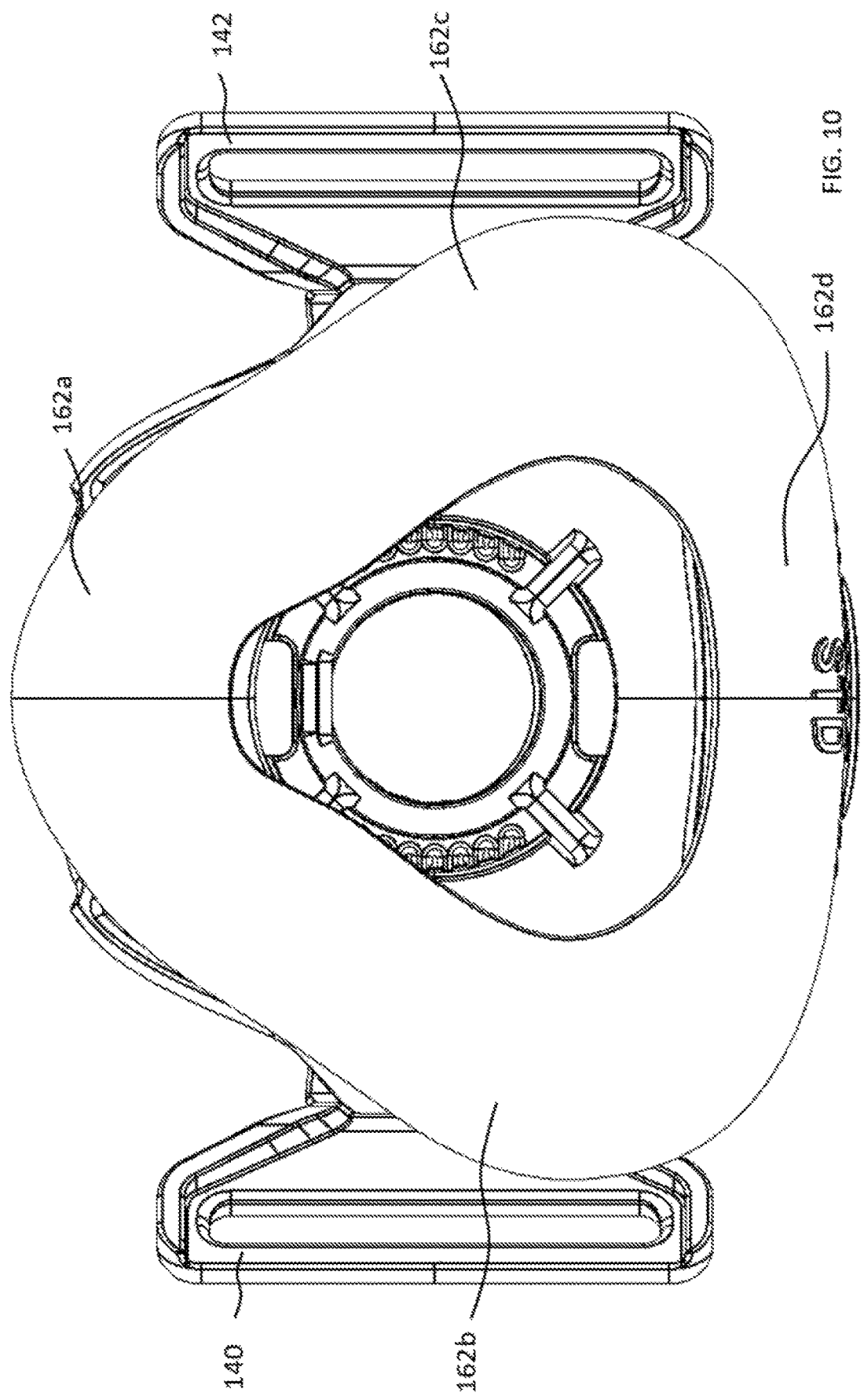
FIG. 10 is a front view of a respiratory mask, in accordance with an embodiment of the present invention.

The buffering piece 162 may be divided into several areas. Please refer to FIG. 10, a front view of a respiratory mask in accordance with an embodiment of the present invention. As depicted in FIG. 10, within the buffering piece 162 there may be defined a nasal bridge portion 162a, a left cheek portion 162b, a right cheek portion 162c, and a lip portion 162d, which together encloses the nose containing room. When the user puts on the respiratory mask 1, their nasal bridge is in contact with the portion 162a, their left nasal ala and left cheek with the portion 162b, their right nasal ala and right cheek with the portion 162c, and their philtrum (the area between the nose and the mouth) with the lip portion 162d.

Figure 11:
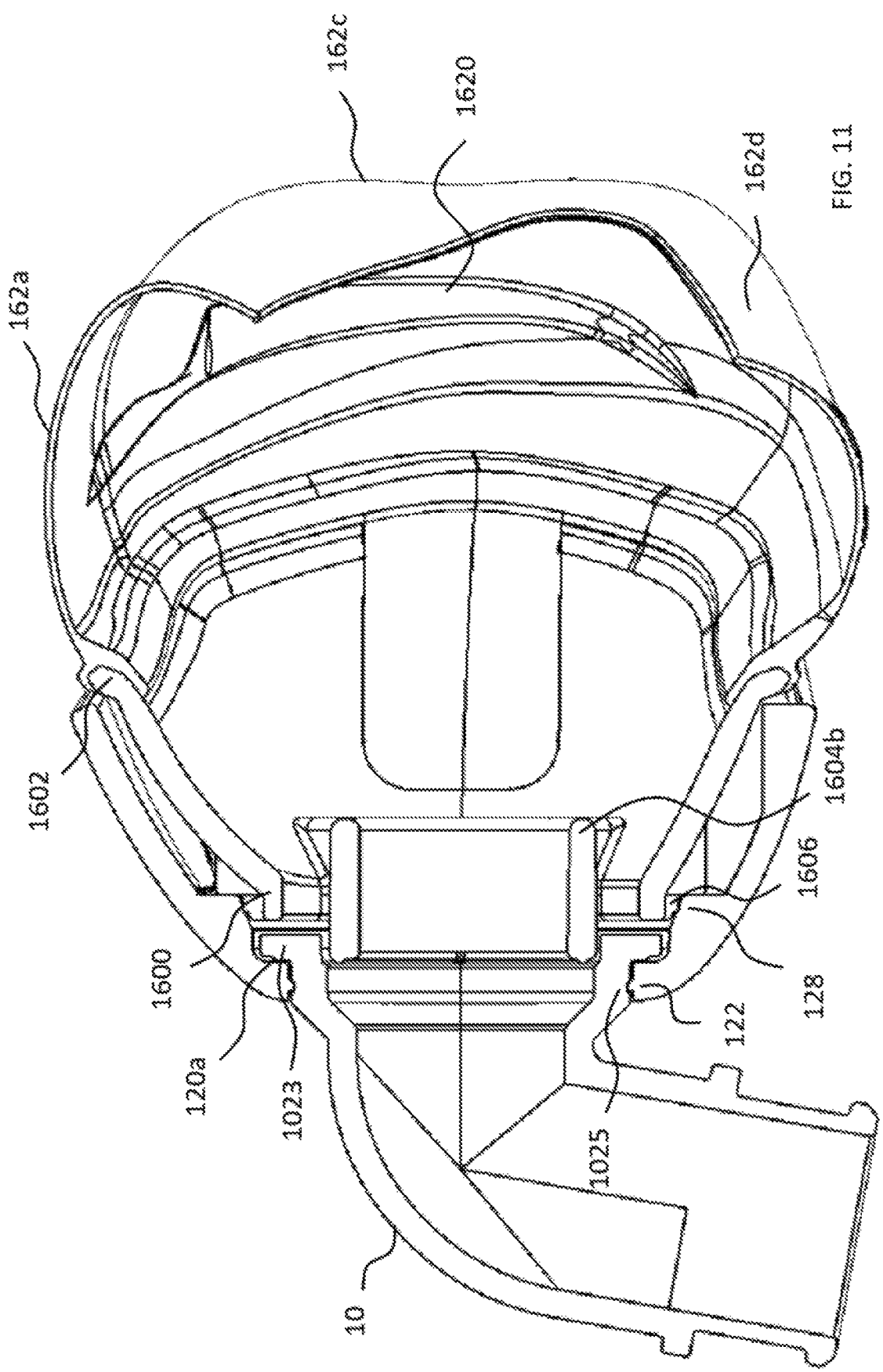
FIG. 11 is a cross section of a respiratory mask along the AA line, in accordance with the embodiment associated with FIG. 1.

In one example, there are disposed a symmetrical pair (a first and a second) of buffering grooves on the inside the buffering piece 162. One of the buffering grooves is situated at the left cheek portion 162b and stretches toward the lip portion 162d, while the other is situated at the right cheek portion 162c and stretches toward the lip portion 162d. The buffering grooves are not readily observable from the outside. For distilled illustration of them, please refer to FIG. 11, a cross section of a respiratory mask along the AA line, in accordance with the embodiment associated with FIG. 1. As depicted in FIG. 11, the buffering groove 1620 stretches from the right cheek portion 162c to the lip portion 162d, and is more or less taper (but not necessarily so), being wider at the right cheek portion 162c than at the lip portion 162d. The buffering groove 1620 is a thinned part of the buffering piece 162. More is chipped away from the inner wall of the right cheek portion 162c; the closer to the lip portion 162d, the less is chipped away. The thinned part of the buffering piece 162 is even more elastic and supple and puts less pressure on the user's face, giving the buffering piece 162 more adaptability to facial contours.

Juxtaposed with preceding figures, FIG. 11 clearly shows that the positioning portions 122 and 1025 are joggled to connect the curved pipe body 100 with the shell 12; that the blocking portions 1023 and 1024, in contact with the supporting plane 120a, prevent the air pipe assembly 10 from being pulled out of the shell 12; and that the airtight ring body 1606, disposed outside the base body 160 and encircling the base intake portion 1600, touches the airtight structure 128, so that most of the airflow fed from the curved pipe body 100 only enters the interior of nose cushion assembly 16 through the air intake zone 1604c enclosed by partitioning wall 1604b. It is also inferable from FIG. 11 that the partitioning wall 1604b should be tall enough to stretch into the connection portion 102 and get close to the curved pipe body 100, thereby reducing loss of the airflow fed therefrom. A partitioning wall 1604b tall enough also helps routing the air. In one example, the partitioning wall 1604b may be 5 mm, 7.5 mm, 10 mm, 12.5 mm, or 15 mm tall. The present embodiment does not prescribe said tallness apart from the requirement that the partitioning wall 1604b not obstruct the assembling of the shell 12 and the air pipe assembly 10 and general usage of the respiratory mask 1.

Figure 12:
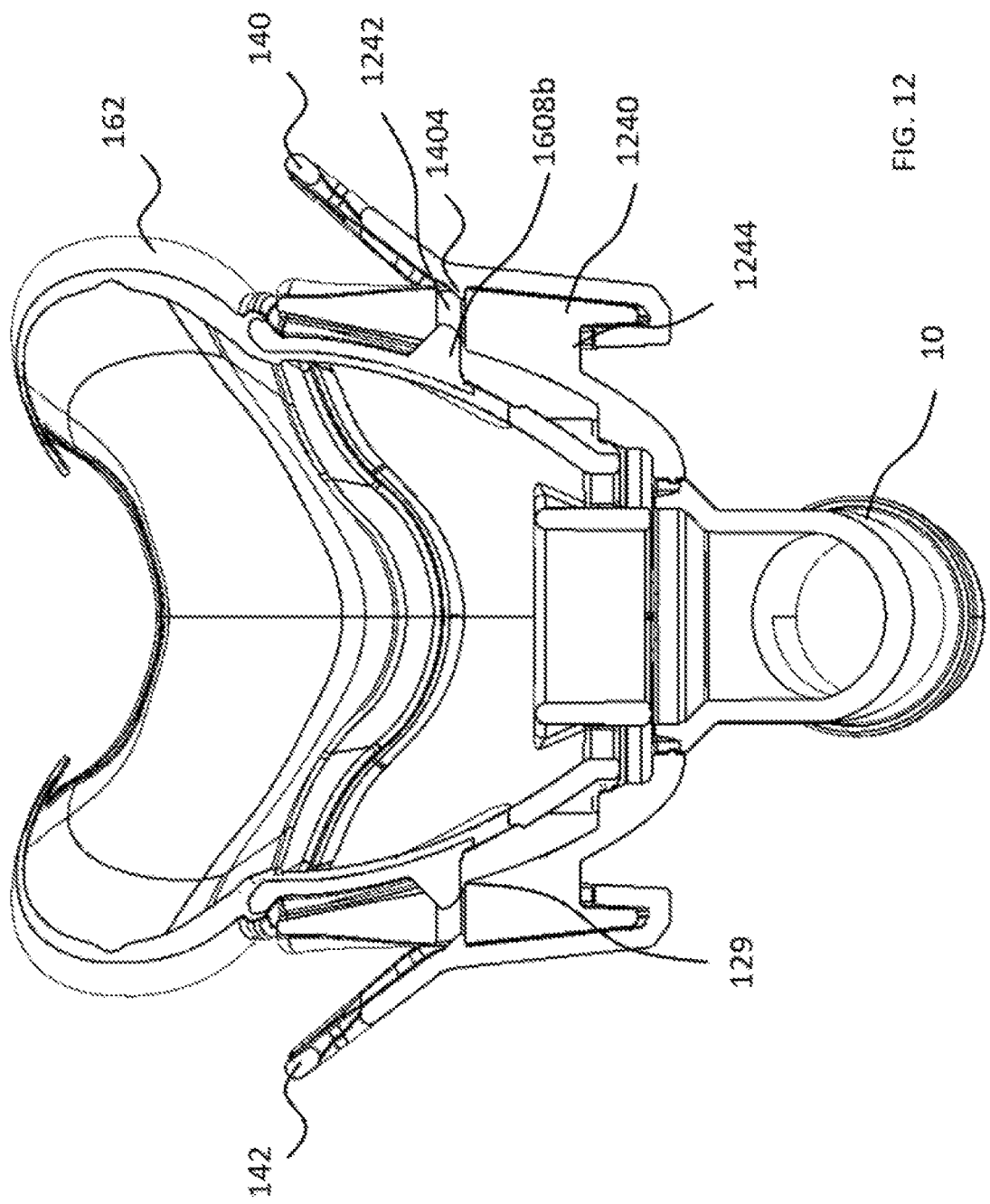
FIG. 12 is a cross section of a respiratory mask along the BB line, in accordance with the embodiment associated with FIG. 1
Figure 13:
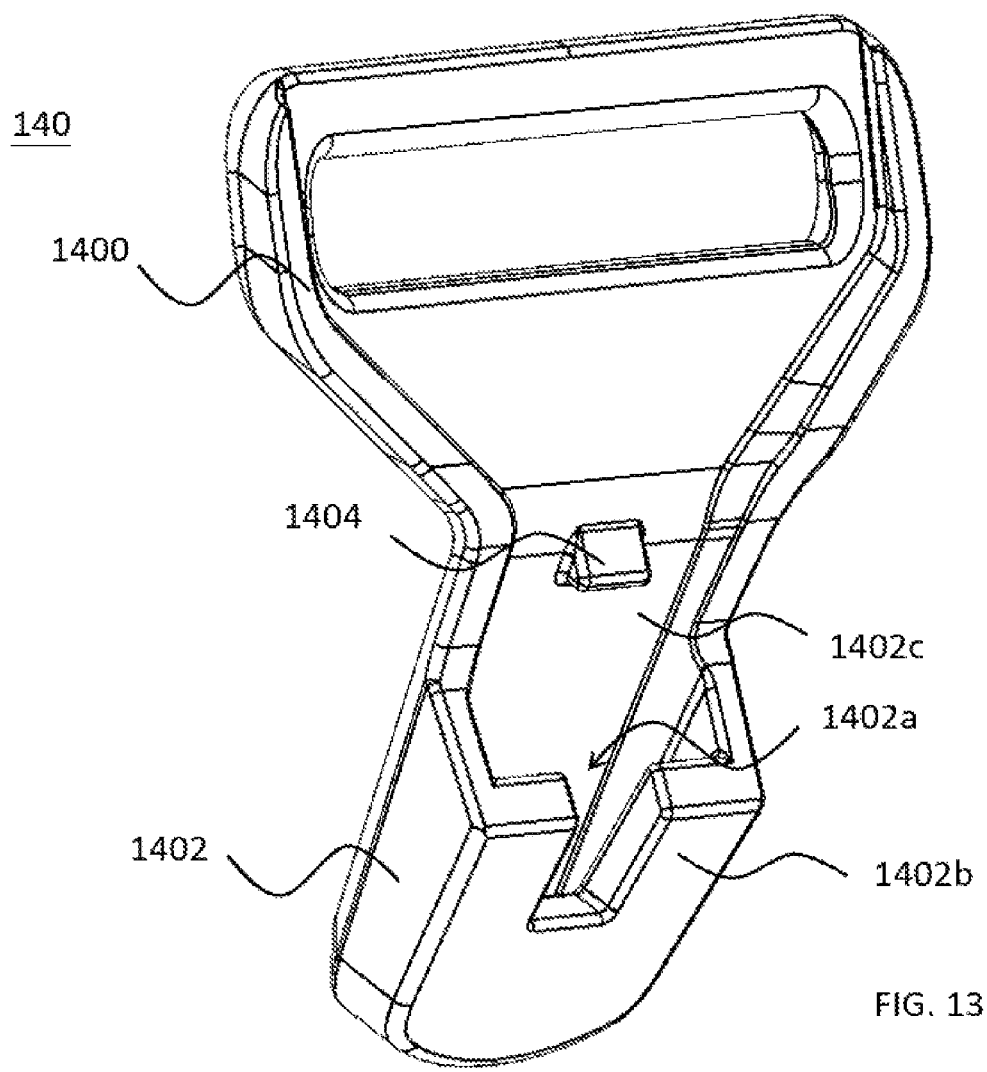
FIG. 13 is a stereogram of a bent plate, in accordance with an embodiment of the present invention.
Figure 14:
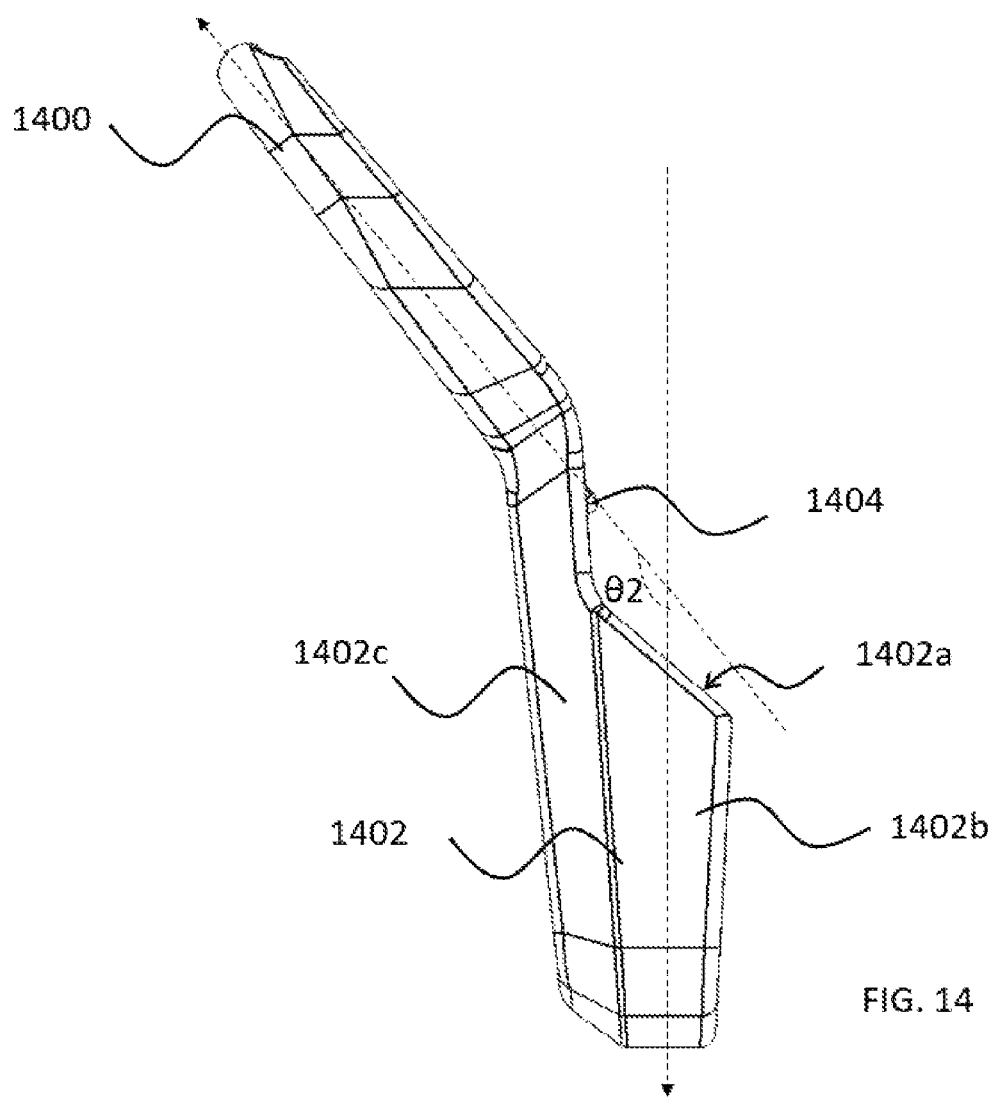
FIG. 14 is a side view of a bent plate, in accordance with an embodiment of the present invention.

At the shell 12 there may be further disposed the bent plates 140 and 142. For distilled illustration of their construction and functionality, using the bent plate 140 as a representative, please refer to FIGS. 12 through 14 in conjunction. In accordance with the embodiment associated with FIG. 1, FIG. 12 is a cross section of a respiratory mask along the BB line, while FIGS. 13 and 14 are a stereogram and a side view of a bent plate, respectively. As depicted in the figures, the respiratory mask 1 includes the bent plates 140 and 142, which are more or less identical in terms of shape and appearance.

At one end of the bent plate 140 there is disposed a ring portion 1400 (first ring portion), and at the other end a slot 1402 (first slot). The bend plate 140 further includes a plate positioning piece 1404 (first plate positioning piece). In one example, the bent plate 140 can be assembled with the buckling portion 124 of FIGS. 5 and 6. Specifically, the tongue 1240 can be inserted into the slot 1402, and the plate positioning piece 1404 can be joggled with the concavity 1242. A person skilled in the art would acknowledge that, once the tongue 1240 is inserted into the slot 1402, the bent plate 140 cannot be detached by reversing the act. This is because the plate positioning piece 1404 blocks the path of extraction along the insert direction. Hence when the user is lying on his or her side, and the pillow rubs against the bent plate 140, the bent plate 140 is actually prevented from falling away from the buckling portion 124 by accident.

There are practical advantages in the plate 140 being bent, one of which is that it reduces the discomfort caused by or eliminates the fact that the user's face touches the bent plate 140 directly, and another of which is that it facilitates quick disassembling of the bent plate 140 and the buckling portion 124. For instance, the direction by which the tongue 1240 is inserted into the slot 1402 differs from that by which the ring portion 1400 stretches, and the two directions form a bend angle θ2. The user may take the ring portion 1400 or the head strap assembly connected to it, pull outward (toward the exterior of the shell 12), and detach the plate positioning piece 1404 from the concavity 1242. The bent plate 140 can then be easily separated from the buckling portion 124. The present embodiment does not prescribe the bend angle θ2, which in one example may be 120°, 135°, 150°, or 165°.

The slot 1402 may consist of an upper slot panel 1402c (first upper slot panel) and a lower slot panel 1402b (first lower slot panel), the panels 1402b and 1402c enclosing a slot vacuity 1402a. The tongue 1240 is contained in the slot vacuity 1402a when the bent plate 140 is assembled with the buckling portion 124. It is inferable from the figures that the ring portion 1400 is disposed at the upper slot panel 1402c, and that the lower slot panel 1402b is of a certain shape (first shape). The shape of the lower slot panel 1402b corresponds to the aligning piece 1244 of the buckling portion 124, so that the bent plate 140 and the buckling portion 124 may be conveniently assembled. In one example, the lower slot panels of the bent plates 140 and 142 each have their own shapes. As a foolproof mechanism, the disagreeing shapes prevent the user from assembling a bent plate with an unmatched buckling portion. In another example, the lower slot panels of the bent plates 140 and 142 mirror each other shape-wise and, in conjunction with the aligning pieces 1244 and 1264, are configured to direct the tongues 1240 and 1260 into the slots The ring portions of the bent plates 140 and 142 may be connected to the head strap assembly. Please refer to FIG. 15, a diagram of a head strap assembly in accordance with an embodiment of the present invention. As depicted in FIG. 15, the head strap assembly 18 comprises a supporting strap 180 (first supporting strap), a supporting strap 182 (second supporting strap), and a supporting strap 184 (third supporting strap). The following description uses the supporting strap 180 as a representative for the straps 180 and 182 are structurally symmetrical. The supporting strap 180 includes a branch 1801 (first branch), a branch 1802 (second branch), and a branch 1803 (third branch). The branch 1801 connects respectively with the branches 1802 and 1803. In one example, the branch 1801 is detachably connected to the ring portion 1400 of the bent plate 140; specifically, the branch 1801 is wound through the ring portion 1400 and secured by means of a touch fastener (velcro), a button, or similar, so that it does not unravel. It is also feasible to sew together the ring portion 1400 and the branch 1801; person skilled in the art would see that unsewing and resewing the two are no incredible feat.

The directions by which the branches 1801 and 1802 respectively stretch form an strap angle θ3 (first strap angle), whereas the directions by which the branches 1801 and 1803 respectively stretch form an strap angle θ4 (second strap angle). The strap angles θ3 and θ4 amount to less than 90°, though it is not prescribed which of the two is greater. In one example, the strap angle θ4 is greater than the strap angle θ3. Meanwhile, the supporting strap 184 includes branches 1840 and 1842. The branch 1840 is configured to connect the branches 1802 and 1803 of the supporting strap 180, and the branches 1822 and 1823 of the supporting strap 182. The branch 1840 is made of firmer material such as multilayer nonwoven fabrics. In contrast, the branch 1842 may be more elastic and made of, say, stretch fabrics. The resulting combination of the branches 1840 and 1842 enables the supporting strap 184 to secure the supporting straps 180 and 182 and to fasten the user's head.

To summarize: The present invention provides a respiratory mask that is more comfortable to wear and wherein the airways and circulation are improved. The respiratory mask as provided can securely cover its user's mouth or nose, reduce the possibility that the user let loose the mask through an inadvertent touch, and can be taken off and disassembled quickly.

What is claimed is:

1. A respiratory mask having a nose cushion assembly, the nose cushion assembly comprising:
    a base body having a base intake portion and a base connection portion, and an air routing piece disposed inside the peripheral of the base intake portion and having a partitioning wall and a wall connection piece; and
    a buffering piece, disposed outside the base body, connecting the base connection portion and enclosing a nose containing room, the nose containing room connecting the inside of the base body;
    wherein the base intake portion and the base connection portion are different side openings of the base body;
    wherein the wall connection piece is disposed outside the partitioning wall and connects the base intake portion and the partitioning wall;
    wherein the inside of the partitioning wall encloses an air intake zone, the air intake zone is approximately at the center of the base intake portion, and an air outtake zone is defined between the partitioning wall and the base intake portion.

2. The respiratory mask according to claim 1, wherein an intake plane is defined within the base intake portion, and part of the partitioning wall juts out of the base body past the intake plane.

3. The respiratory mask according to claim 1, wherein the base intake portion connects with an airtight ring body, and wherein the airtight ring body is disposed outside the base body and encircles the base intake portion.

4. The respiratory mask according to claim 3, wherein the base body further comprises a base positioning piece disposed at the outside of the base body and between the base intake portion and the base connection portion, the base positioning piece has a positioning cantilever, a base positioning buckle, and a buffering pad, the base positioning buckle is disposed at the positioning cantilever, and the buffering pad is underneath the positioning cantilever.

5. The respiratory mask according to claim 4, further comprising:
    an air pipe assembly comprising a curved pipe body and a first connection portion, the first connection portion having a first through hole and a first ventilating portion; and
    a shell connected detachably with the first connection portion and having an airtight structure and a base positioning slot;

wherein the first ventilating portion has a plurality of concavities on the connection portion;

wherein an end of the curved pipe body connects with the first connection portion, and together the curved pipe body and the first through hole form an air passage;

wherein the airtight structure is disposed at the outside of the shell, and the base positioning slot opens at the inside of the shell;

wherein the airtight structure is an annular structure encircling a second through hole of the shell;

wherein the base positioning piece is detachably lodged in the base positioning slot when the nose cushion assembly is assembled with the shell.

6. The respiratory mask according to claim 5, wherein when the nose cushion assembly is assembled with the shell, together the curved pipe body, the first through hole, and the air routing piece form an air passage passing through the air intake zone enclosed by the inside of the partitioning wall.

7. The respiratory mask according to claim 5, wherein the first ventilating portion corresponds to the air outtake zone between the partitioning wall and the base intake portion when the nose cushion assembly is assembled with the shell.

8. The respiratory mask according to claim 5, wherein the first connection portion further comprises a second ventilating portion, having a plurality of concavities on the connection portion, the first ventilating portion and the second ventilating portion are symmetrically disposed within the first connection portion; the first connection portion defines a first surface, a lateral facet, and a second surface, the first surface is adjacent to the lateral facet; and the first ventilating portion and the second ventilating portion stretch from the first surface to the second surface and are exposed at the first surface and the lateral facet.

9. The respiratory mask according to claim 8, wherein the first connection portion further defines an incline adjacent to the lateral facet, the lateral facet is between the first surface and the incline, and the first ventilating portion is exposed at the incline.

10. The respiratory mask according to claim 9, wherein the first ventilating portion is more exposed at the first surface than at the incline.

11. The respiratory mask according to claim 8, wherein each of the perimeters of the first surface and the second surface approximately forms a circle, and the area enclosed by the perimeter of the first surface is larger than the area enclosed by the perimeter of the second surface.

12. The respiratory mask according to claim 8, wherein the first connection portion has further a first positioning portion and a first blocking portion, the first positioning portion is a groove and exposed at the lateral facet, the first blocking portion is disposed at the first surface, the first positioning portion and the first blocking portion are at different sides of the first surface, the first blocking portion stretches from the first surface, and part of the first blocking portion is outside the perimeter of the first surface.

13. The respiratory mask according to claim 12, wherein the shell further comprises a second positioning portion rotatably mounted at the first positioning portion, the first ventilating portion rotates relative to the shell and the curved pipe body rotates relative to the shell when the first positioning portion rotates relative to the second positioning portion.

14. The respiratory mask according to claim 13, wherein the lateral facet being adjacent to both the first surface and the incline, and wherein an end of the first ventilating portion is exposed at the first surface, and another end of the first ventilating portion is exposed at the incline.

15. The respiratory mask according to claim 12, wherein a second positioning portion is disposed at the second through hole, and the first connection portion is contained in the second through hole.

16. The respiratory mask according to claim 15, wherein the second through hole has a first supporting plane, at least part of the first blocking portion touches the first supporting plane, and the first surface and the first supporting plane are approximately coplanar.

17. The respiratory mask according to claim 5, wherein the shell further comprises a first buckling portion, the first buckling portion has a first tongue, having a first end and a second end, the first end has a first thickness and connects with an outer surface of the shell, the second end has a second thickness and stretches along a first direction, and the first thickness is greater than the second thickness.

* * * * *